United States Patent [19]

Gilman et al.

[11] Patent Number: 5,675,079
[45] Date of Patent: Oct. 7, 1997

[54] APPARATUS FOR MEASURING THE CRUSH RECOVERY OF AN ABSORBENT ARTICLE

[75] Inventors: Thomas Harry Gilman, Appleton; Peter Douglas Honer, Neenah, both of Wis.

[73] Assignee: Kimberly-Clark Worldwide, Inc., Neenah, Wis.

[21] Appl. No.: 474,841

[22] Filed: Jun. 7, 1995

[51] Int. Cl.$^6$ ............................................. G01N 3/08
[52] U.S. Cl. ............................................. 73/118
[58] Field of Search ............................. 73/818–823, 852

[56] References Cited

U.S. PATENT DOCUMENTS

| | | | |
|---|---|---|---|
| 1,452,810 | 4/1923 | Moore et al. | 73/823 |
| 2,295,016 | 9/1942 | Scribner | 128/290 |
| 2,295,439 | 2/1942 | Voigtman | 128/284 |
| 2,468,876 | 4/1949 | Hermanson | 128/290 |
| 2,582,344 | 1/1952 | Milton | 128/290 |
| 2,772,678 | 12/1956 | Leupold | 128/290 |
| 2,833,283 | 5/1958 | Spahr et al. | 128/290 |
| 2,960,089 | 11/1960 | Harwood et al. | 128/290 |
| 3,067,747 | 12/1962 | Wolterding et al. | 128/296 |
| 3,143,113 | 8/1964 | Mills | 128/290 |
| 3,343,543 | 9/1967 | Glassman | 128/290 |
| 3,375,827 | 4/1968 | Bletzinger et al. | 128/290 |
| 3,403,681 | 10/1968 | Hoey et al. | 128/290 |
| 3,441,023 | 4/1969 | Rijssenbeek | 128/287 |
| 3,463,154 | 8/1969 | Hendricks | 128/287 |
| 3,477,433 | 11/1969 | Dillon | 128/290 |
| 3,525,337 | 8/1970 | Simons | 128/290 |
| 3,593,717 | 7/1971 | Jones, Sr. et al. | 128/290 |
| 3,654,929 | 4/1972 | Nilsson et al. | 128/287 |
| 3,667,468 | 6/1972 | Nystrand et al. | 128/290 |
| 3,699,966 | 10/1972 | Chapuis | 128/290 R |
| 3,746,592 | 7/1973 | Nystrand et al. | 156/202 |
| 3,749,627 | 7/1973 | Jones, Sr. | 156/268 |
| 3,759,262 | 9/1973 | Jones, Sr. | 128/290 R |
| 3,771,525 | 11/1973 | Chapuis | 128/290 R |
| 3,865,112 | 2/1975 | Roeder | 128/290 R |
| 3,897,784 | 8/1975 | Fitzgerald | 128/290 R |
| 3,932,322 | 1/1976 | Duchane | 260/17.4 |
| 3,939,838 | 2/1976 | Fujinami et al. | 128/290 R |
| 3,954,107 | 5/1976 | Chesky et al. | 128/290 R |
| 4,029,101 | 6/1977 | Chesky et al. | 128/290 R |
| 4,057,061 | 11/1977 | Ishikawa et al. | 128/284 |

(List continued on next page.)

FOREIGN PATENT DOCUMENTS

| | | |
|---|---|---|
| 0 572 033 | 12/1993 | European Pat. Off. . |
| 40 13 015 A1 | 4/1990 | Germany ............. G01B 5/06 |
| 1333081 | 10/1973 | United Kingdom . |
| WO 91/09583 | 7/1991 | WIPO . |
| WO 94/26221 | 11/1994 | WIPO . |
| WO 95/10996 | 4/1995 | WIPO . |

OTHER PUBLICATIONS

Copending patent application entitled "An Absorbent Article Having a Non-Absorbent, Resilient Layer" having U.S.S.N. 891,361 filed May 29, 1992 (K-C File No. 10,293).

*Primary Examiner*—Robert Raevis
*Attorney, Agent, or Firm*—Thomas J. Connelly

[57] ABSTRACT

An apparatus is disclosed for measuring the crush recovery of an absorbent article. The apparatus includes a tester having first and second arms, at least one of which is movable. The apparatus also includes a first frame member attached at one end to the first arm of the tester. The first frame member has a shoulder with a first wand extending outwardly therefrom. The apparatus further includes a second frame member attached at one end to the second arm of the tester. The second frame member has a shoulder with a second wand extending outwardly therefrom. The first and second frame members are interleaved such that the first and second wands are spaced apart to enable an absorbent article to be positioned therebetween. Movement of the first frame member relative to the second frame member causes the absorbent article to be crushed in a sideways direction between the shoulders. As the relative movement of the frame members is reversed, the absorbent article is able to expand outward toward its original transverse dimension. The amount of sideways recovery is measured as the "crush recovery" value.

17 Claims, 3 Drawing Sheets

U.S. PATENT DOCUMENTS

| | | | |
|---|---|---|---|
| 4,079,739 | 3/1978 | Whitehead | 128/290 R |
| 4,100,324 | 7/1978 | Anderson et al. | 428/288 |
| 4,276,338 | 6/1981 | Ludwa et al. | 428/137 |
| 4,315,507 | 2/1982 | Whitehead et al. | 128/287 |
| 4,357,939 | 11/1982 | Jackson et al. | 128/290 R |
| 4,372,312 | 2/1983 | Fendler et al. | 128/290 R |
| 4,397,644 | 8/1983 | Matthews et al. | 604/378 |
| 4,531,945 | 7/1985 | Allison | 604/378 |
| 4,551,142 | 11/1985 | Kopolow | 604/368 |
| 4,568,341 | 2/1986 | Mitchell et al. | 604/368 |
| 4,623,340 | 11/1986 | Luceri | 604/385 R |
| 4,627,848 | 12/1986 | Lassen et al. | 604/370 |
| 4,631,062 | 12/1986 | Lassen et al. | 604/385 R |
| 4,641,534 | 2/1987 | Schneider et al. | 73/821 |
| 4,731,071 | 3/1988 | Pigneul | 604/385 R |
| 4,781,962 | 11/1988 | Zamarripa et al. | 428/138 |
| 4,798,601 | 1/1989 | Shirose et al. | 604/368 |
| 4,798,603 | 1/1989 | Meyer et al. | 604/378 |
| 4,822,668 | 4/1989 | Tanaka et al. | 428/283 |
| 4,840,070 | 6/1989 | Ralfs et al. | 73/818 |
| 4,846,824 | 7/1989 | Lassen et al. | 604/385.1 |
| 4,892,534 | 1/1990 | Datta et al. | 604/370 |
| 4,908,026 | 3/1990 | Sukiennik et al. | 604/378 |
| 4,973,325 | 11/1990 | Sherrod et al. | 604/368 |
| 5,009,653 | 4/1991 | Osborn, III | 604/385.1 |
| 5,037,412 | 8/1991 | Tanzer et al. | 604/359 |
| 5,048,347 | 9/1991 | Knowles | 73/821 |
| 5,090,249 | 2/1992 | Bielewicz | 73/822 |
| 5,135,521 | 8/1992 | Luceri et al. | 604/383 |
| 5,209,124 | 5/1993 | Graudejus et al. | 73/821 |
| 5,300,055 | 4/1994 | Buell | 604/385.1 |
| 5,324,278 | 6/1994 | Visscher et al. | |
| 5,394,753 | 3/1995 | Moriyoshi | 73/818 |

APPARATUS FOR MEASURING THE CRUSH RECOVERY OF AN ABSORBENT ARTICLE

FIELD OF THE INVENTION

This invention relates to a thin absorbent article for absorbing and retaining human exudate and an apparatus for measuring the crush recovery of an absorbent article. More specifically, this invention relates to a thin sanitary napkin which can reduce body fluid leakage during use.

BACKGROUND OF THE INVENTION

Absorbent articles such as sanitary napkins, incontinent garments, incontinent shields, and the like, are designed to be worn adjacent to a woman's pudendum to absorb body fluids such as menses, blood, urine and other excrements. Some of these products are designed with sufficient absorbent capacity to be worn during the menstrual period while others are intended to be worn before and after the menstrual period to absorb small quantities of body fluid. Today, thin absorbent articles having an overall thickness of about five millimeters or less are preferred by a large number of women. Younger women in particular like to wear thin absorbent articles because they are more discreet under tight fitting clothing and do not restrict body movement as do some thick pads.

In order to provide the consumer with thin absorbent articles which also contain sufficient absorbent capacity, some manufacturers have added superabsorbents to their products. While superabsorbents do have the ability to absorb large quantities of body fluid if provided with sufficient time to absorb the fluid, most suffer from two major drawbacks. First, many superabsorbents exhibit slow fluid take-up rates which provide little benefit to reducing leakage during periods when the absorbent article is insulted with a large quantity of body fluid. This leakage problem becomes more pronounced in thin sanitary napkins because any body fluid which pools on the bodyside cover has a greater tendency to run off the side edges before it can be absorbed into the underlying absorbent. Second, most superabsorbents are expensive and their use increases the overall cost of the finished article.

Another deficiency usually exhibited by thin absorbent articles is that some are relatively stiff and therefore can feel uncomfortable when positioned between a user's thighs. Such a feature becomes more pronounced on women who's anatomy have a very narrow distance between the thighs. Preferably, thin absorbent articles should be both pliable and comfortable to wear.

Now, a thin absorbent article has been invented which contains a multi-layered absorbent structure which reduces leakage and is very comfortable to wear.

SUMMARY OF THE INVENTION

Briefly, this invention relates to a thin absorbent article, such as a thin sanitary napkin, which is designed to reduce leakage of body fluid during use. An apparatus for measuring the crush recovery of an absorbent article is also disclosed. The absorbent article includes a liquid-permeable cover, a liquid-impermeable baffle and an absorbent positioned between the cover and the baffle. The absorbent article has a crush recovery value of at least about 15 mm, a wet load value of at least about 300 grams, a stress value of less than about 100 grams/mm, and a thickness of less than about 5 millimeters.

An apparatus for measuring the crush recovery of an absorbent article is also described. The apparatus includes a tester having first and second arms, of which at least one is movable. The apparatus also includes a first frame member attached at one end to the first arm. The first frame member has a shoulder with a first wand extending outwardly therefrom. The apparatus further includes a second frame member attached at one end to the second arm. The second frame member has a shoulder with a second wand extending outwardly therefrom. The first and second frame members are interconnected such that the first and second wands are spaced apart to enable an absorbent article to be positioned therebetween. Movement of the first frame member away from the second frame member causes the absorbent article to be crushed in a sideways direction between the shoulders. The applied force is then removed and the absorbent article is able to expand outward toward its original transverse dimension. The amount of sideways recovery is referred to as "crush recovery" and this value is measured and recorded.

The general object of this invention is to provide a thin absorbent article for absorbing and retaining human exudate and an apparatus for measuring the crush recovery of an absorbent article. A more specific object of this invention is to provide a thin sanitary napkin which can absorb and retain body fluid, including menses, while reducing leakage of body fluid during use.

Another object of this invention is to provide a thin absorbent article which has a thickness of less than about five millimeters.

A further object of this invention is to provide an apparatus for crushing sideways and then measuring and recording the amount the absorbent article could recover.

Still another object of this invention is to provide a thin absorbent article having an absorbent formed from a multi-layered structure of fine pore fabric.

Still further, an object of this invention is to provide an inexpensive thin absorbent article which is void of superabsorbent.

Other objects and advantages of the present invention will become more apparent to those skilled in the art in view of the following description and the accompanying drawings.

DETAILED DESCRIPTION OF THE PREFERRED EMBODIMENT

Figure 1:
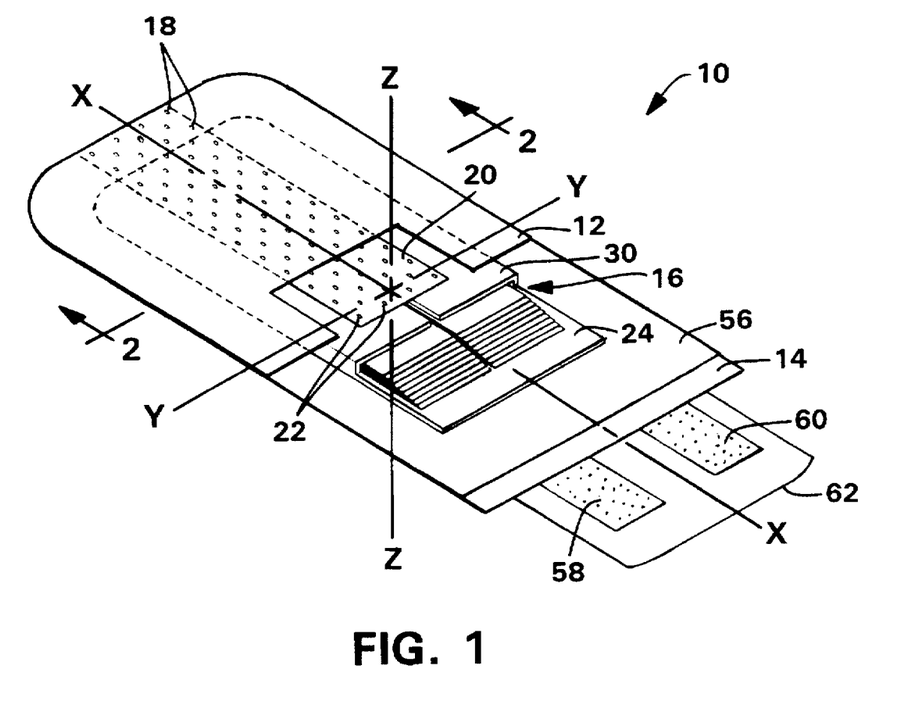
FIG. 1 is a partially sectioned perspective view of a thin absorbent article having a multi-layered absorbent structure.
Figure 2:
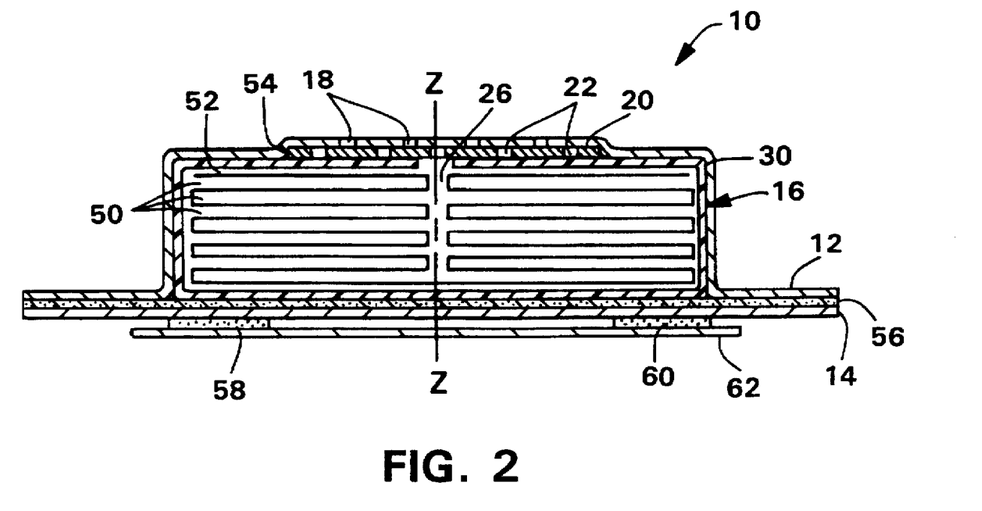
FIG. 2 is a cross-sectional view of the thin absorbent article taken along line 2—2 of FIG. 1.

Referring to FIGS. 1 and 2, a thin absorbent article 10 is shown which is depicted as a sanitary napkin. A sanitary napkin is designed to be worn by a woman to absorb body fluids such as menses, blood, urine and other excrements. A sanitary napkin is also referred to as a catamenial pad or a feminine pad. Although the thin absorbent article 10 will be described with reference to a sanitary napkin, it can also encompass other articles such as an incontinent garment, incontinent shields, and the like. Furthermore, the thin absorbent article 10 can be used either alone or in combination with underwear, menstrual panties, or specially designed belts, straps or harnesses.

By thin absorbent articles is meant articles having an overall thickness of less than about five millimeters (mm). More preferably, the thin absorbent articles will have a thickness of between about 2 mm to about 5 mm. The precise method used to determine the thickness of a thin absorbent article will be described in greater detail below.

The thin absorbent article 10, when in the form of a sanitary napkin 10, is an elongated article having a central longitudinal x-axis, denoted X—X and a central transverse y-axis, denoted Y—Y. The transverse y-axis is perpendicularly orientated relative to the longitudinal x-axis. The sanitary napkin 10 has a length of between about 150 mm to about 300 mm and a width of between about 50 mm to about 125 mm. The sanitary napkin 10 can have a generally rectangular shape with rounded ends, or it can have an elongated oval shape, an hourglass shape, a dogbone shape, a racetrack shape or some other configuration.

The sanitary napkin 10 can include a liquid-permeable cover 12, a liquid-impermeable baffle 14 and an absorbent 16 positioned between the cover 12 and the baffle 14. Typically, the cover 12 and the baffle 14 cooperate to enclose the absorbent 16. The cover 12 is designed to contact the body of the wearer and can be constructed of a woven or nonwoven material which is easily penetrated by body fluid. The cover 12 can also be either natural or synthetic fibers. Suitable materials include bonded carded webs of polyester, polypropylene, polyethylene, nylon, or other heat-bondable fibers. Other polyolefins, such as copolymers of polypropylene and polyethylene, linear low-density polyethylene, finely-perforated film webs and net materials, also work well. A particular preferred material is a composite of an apertured thermoplastic film positioned above a nonwoven fabric material. Such composite material can be formed by extrusion of a polymer onto a web of spunbond material to form an integral sheet. One example of this is an apertured thermoplastic film bonded to a spunbond material. This material exhibits a smooth and soft outer surface which is not irritating to the wearer's skin and yet has a cushioned feel because of it's bulk.

Another preferred material for the cover 12 is a spunbond web of polypropylene. The web can contain from between about 1 percent to about 6 percent of titanium dioxide pigment to give it a clean, white appearance. A uniform thickness of spunbond is desirable because it will have sufficient strength, after being perforated in the longitudinal direction, to resist being torn or pulled apart during use. The most preferred polypropylene webs have a weight of between about 18 to about 40 grams per square meter. An optimum weight is between about 30 to about 40 grams per square meter.

The liquid-impermeable cover 12 can also contain a plurality of apertures 18 formed therethrough. The apertures 18 can be arranged uniformly or randomly over either the entire surface of the cover 12 or over a portion of the surface of the cover 12. For example, the apertures 18 can be arranged in a band having a width of between about 0.5 of an inch to about 2 inches (about 12.7 mm to about 50.8 mm) which extend along the central longitudinal x-axis. The band of apertures 18 can run the entire length of the sanitary napkin 10 or be present over only a portion of the overall length. The apertures 18 are intended to facilitate the movement of body fluid which is deposited onto the cover 12 to penetrate down into the absorbent 16.

The size and shape of the apertures 18 can vary, however, for menstrual fluid in particular, the apertures 18 should have a round or circular cross-sectional area. Other shapes such as an oval, an ellipse, etc. can also be used. Generally, each apertures 18 will be a hole, gap, slit, orifice, space, division, or opening that will range in size from about 0.3 mm to about 5.0 mm. At least one of the apertures 18 formed in the cover 12 should have a diameter within this range. Preferably, a majority of the apertures 18 will have a diameter greater than about 0.3 mm. If an aperture 18 is not round, such that it does not have a diameter, then the surface area of the opening should be equivalent to or greater than that of a circle having a diameter of about 0.3 mm. In addition, each of the apertures 18 can be spaced apart from an adjoining aperture 18 by an equal distance or by various distances. The apertures 18 can be spaced from an adjacent aperture 22 by almost any distance but this distance should be at least about 0.3 mm or more. The size of the aperture 18 can effect to a certain extent the closeness at which an adjacent aperture 18 can be located. Although the apertures 18 are not essential, they do provide a functional advantage which should not be overlooked. The presence of the apertures 18 helps the body fluid to quickly migrate into the absorbent 16 and therefore makes the sanitary napkin 10 very comfortable to wear. By allowing the body fluid to pass quickly through the cover 12, the absorbent article 10 tends to stay drier along with the body of the wearer. Quick migration of the body fluid into the absorbent article 10 also helps to reduce fluid leakage.

The liquid-impermeable baffle 14 permits the passage of air or vapor out of the sanitary napkin 10 while blocking the passage of body fluid. The baffle 14 can be made from any material having these properties. The baffle 14 can also be constructed from a material that will block the passage of vapor as well as fluids, if desired. A good material for the baffle 14 is a micro-embossed, polymeric film, such as polyethylene or polypropylene. Bicomponent films can also be used. A preferred material is polyethylene film. Most preferably, the baffle 14 will be comprised of a polyethylene film having a thickness in the range of from about 0.5 mm to about 2.0 mm.

Figure 3:
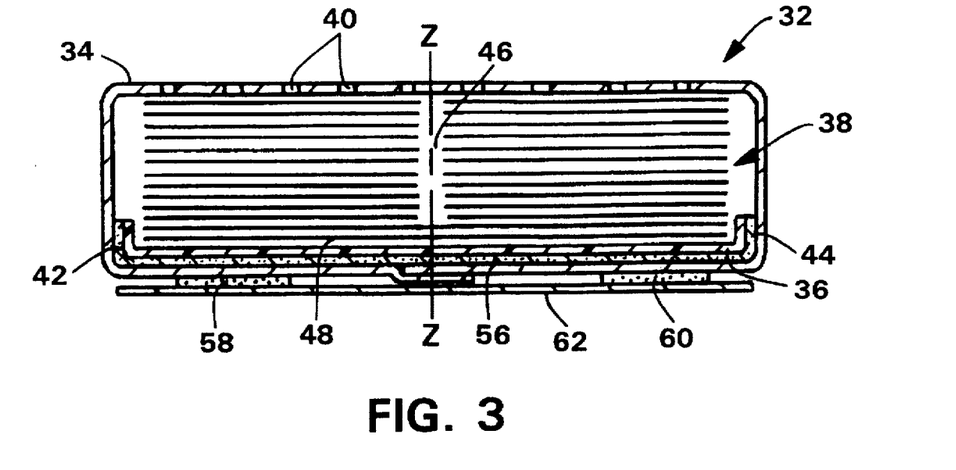
FIG. 3 is a cross-sectional view of another embodiment of a thin absorbent article having a multi-layered absorbent structure formed from a plurality of vertically stacked sheets.

The baffle 14 can be cut to a size and shape which will make it coextensive with the cover 12. When this is done, the cover 12 and the baffle 14 can be bonded in a face to face contact to form a peripheral sealed sanitary napkin, as is depicted in FIG. 1. It is also possible to wrap the cover 12 completely around the absorbent 16, as shown in FIG. 3, and then adhere the cover 12 to the upper surface of the baffle 14. Alternatively, the baffle 14 can be wrapped up along the side edges of the absorbent 16 and then the cover 12 can be wrapped completely around both the baffle 14 and absorbent 16. These and other variations are known to those skilled in the absorbent article art.

The cover 12 and the baffle 14 will cooperate to retain the absorbent 16 therebetween. It should be noted that the baffle 14 does not have to be directly bonded or secured to the cover 12 but can be attached to an intermediate member which in turn is bonded to the cover 12. In either case, the absorbent 16 is intermediate the cover 12 and the baffle 14.

Referring again to FIGS. 1 and 2, a transfer layer 20 having a plurality of apertures 22 formed therethrough is positioned between the cover 12 and the baffle 14. Preferably, the transfer layer 20 is positioned immediately below the cover 12 and is in direct face to face contact therewith. Although the transfer layer 20 is optional, when present, it does provide good fluid movement downward from the cover 12 into the absorbent 16. This downward movement of fluid is parallel to a vertical z-axis, denoted Z—Z. The z-axis is perpendicularly arranged relative to the x and y and axes.

The transfer layer 20 can be constructed from a material that will provide good fluid transfer. Typical materials which can be used for the transfer layer 20 are spunbond, coform and carded webs. One useful material which was tried was a 0.95 ounces per square yard (osy) spunbond which was peach in color. The spunbond contained a plurality of apertures 22 having a diameter of about 0.125 of an inch (about 3.18 mm) which were formed on a grid spacing of about 0.5 of an inch by about 0.375 of an inch (about 12.7 mm by about 9.26 mm). Another preferred material is meltblown polypropylene having a weight of between about 0.2 osy to about 2.0 osy.

It has been noticed that when the transfer layer 20 has a frictional hairy, fibrous surface that it will adhere to the cover 12 and aid in fluid transfer from the cover 12 to the absorbent 16. The transfer layer 20 can be treated to make it hydrophilic. The transfer layer 20 can be a single sheet of about 1.0 osy to about 2.0 osy or be folded to achieve that weight. The thickness of the transfer layer 20 is generally between about 1 mm and 5 mm. The apertures or perforations 22 can be uniformly or randomly arranged throughout the surface of the transfer layer 20. The apertures 22 are coaxially aligned with or be offset from the apertures 18 formed in the cover 12. The apertures 22 can be smaller, larger or of the same size as the apertures 18 which are formed in the cover 12. Generally, each apertures 22 will be a hole, gap, slit, orifice, space, division, or opening that will range in size from about 0.3 mm to about 5.0 mm. Preferably, a majority of the apertures 22 have a diameter greater than about 0.3 mm. If the aperture 22 is not round, such that it does not have a diameter, then the surface area of the opening should be equivalent to or greater than that of a circle having a diameter of about 0.3 mm. The apertures 22 can be spaced from an adjacent aperture 22 by almost any distance but this distance should be at least about 0.3 mm or more. The size of the aperture 22 can effect to a certain extent the closeness at which an adjacent aperture 22 can be located.

Like the apertures 18 formed in the cover 12, the apertures 22 can vary in size and shape. The apertures 22 can have a round, circular, oval, elliptical or some other cross-sectional area. It is also possible to form the apertures 22 as slits which will open in use to a larger size to permit fluid flow therethrough. For most applications, the apertures 22 should be round holes.

The transfer layer 20 may also be colored a different color than the cover 12 and/or the absorbent 16. A light blue, pink or peach color has been found to be desirable as these are pleasing feminine colors. The use of a different color than the absorbent 16 also presents a target for the wearer and will indicate when the sanitary napkin 10 was not placed properly relative to the vagina.

Positioned between the transfer layer 20 and the baffle 14 is the absorbent 16. The absorbent 16 is a multi-layered structure having at least one fluid passage 26 formed therein. The absorbent 16 is free of or void of any superabsorbent material. The absorbent 16 can be formed from a single sheet 24 of an absorbent material which is folded upon itself, such as in an accordion fashion, to obtain the multi-layered structure. The actual method of folding may vary but the idea is to obtain a multi-layered structure having from between about 5 to about 30 vertically stacked, horizontal layers. Preferably, the folded sheet 24 will contain from about 7 to about 15 vertically stacked layers. The absorbent 16 can be made from any suitable absorbent material including wood pulp fluff, rayon, cotton and meltblown polymer, such as polyester, polypropylene or coform. Coform is a meltblown air-formed combination of meltblown polymers, such as polypropylene and absorbent staple fibers, such as cellulose. The above identified absorbent material should be formed into a sheet, web or tissue structure and not be used in loose fibrous form as is the case for many commercially available thick sanitary napkins. A preferred material is wood fluff which has been formed into a tissue sheet because it is low in cost, relatively easy to make and has good absorbency.

The absorbent 16 may also be a composite material comprised of a hydrophilic material that can be formed from various natural or synthetic fibers, wood pulp fibers, regenerated cellulose fibers or cotton fibers, or a blend of pulp and other fibers. A preferred material is a fine pore fabric such a wet-laid, air dried tissue. The absorbent 16 may also be comprised of other well-known materials used in absorbent articles, including cellulose fibers, rayon fibers, cellulose sponge, hydrophilic synthetic sponge, such as polyurethane, and the like.

When tissue is used, it can vary in basis weight, thickness, apparent density, etc. A preferred basis weight is about 30 grams per square meter (gsm), a preferred thickness is about 0.25 mm, and an apparent density is about 0.12 grams per cubic meter. The tissue can be of any size and shape, although for a sanitary napkin, a rectangular configuration with or without rounded corners works fine. For a typical sanitary napkin 10, each tissue sheet 24 can have dimensions which range from between about 2 inches to about 12 inches (about 50.8 mm to about 304.8 mm) in length and from about 1 inch to about 5 inches (about 25.4 mm to about 127 mm) in width. If the tissue sheet 24 is cut or sliced, and then reassembled into the multi-layered absorbent structure 16, it is possible to form the tissue sheet 24 to almost any dimension. It should be noted that each tissue sheet 24 can be a single ply or two or more plies which are assembled to form a single sheet 24. The plies can be assembled by heat and/or pressure, by mechanical means, etc.

The absorbent 16 can also be constructed from a meltblown olefin fabric. Regardless of the type of material used, the absorbent sheet(s) 24 can be treated to be hydrophilic.

Referring again to FIGS. 1 and 2, the multi-layered absorbent structure can be wrapped in a tissue sheet 30. The tissue 30 is beneficial in holding and retaining the multi-layered absorbent structure together.

Referring to FIG. 3, an alternative arrangement for an absorbent article 32 is shown. The absorbent article 32 is again depicted as a sanitary napkin having a liquid-permeable cover 34 and a liquid-impermeable baffle 36 which cooperate to enclose an absorbent 38. The cover 34 still contains apertures 40 which function as the apertures 18 do in FIGS. 1 and 2. However, one noticeable difference is that the cover 34 wraps completely around both the baffle 36 and absorbent 38. A second difference is that the baffle 36 has longitudinal side edges 42 and 44 which extend upward along the sides of the multi-layered absorbent structure 38. The upwardly oriented side edges 42 and 44 assist in preventing fluid leakage from the sanitary napkin 32 during use. A third difference from the embodiment shown in FIGS. 1 and 2 is that the absorbent 38 is formed from a plurality of individual sheets 28 of absorbent material. The sheets 28 are vertically stacked to form a plurality of horizontal layers. The number of sheets 28 in the multi-layered absorbent structure 38 can range from between 5 to 30. Preferably, the number of sheets 28 will range from between 7 to 15, and most preferably, the number of sheets 28 will range from between 8 to 12. Each sheet 28 can be a layer of tissue which has the same thickness, physical properties and functional characteristics as an adjacent layer. Alteratively, each sheet can be constructed to have a different thickness, different physical properties and/or different functional characteristics as an adjacent layer. For ease of manufacture, all the sheets 28 should be essentially the same.

In FIG. 3, the multi-layered absorbent structure has a central passage 46 formed therein which is coaxially aligned with the z-axis. The overall size and shape of each sheet 28 can vary as can the overall width of each sheet, the stacking arrangement for the multiple sheets, the depth of the passage 46, etc. Preferably, the passage 46 will extend completely through all of the sheets 28 and optionally will extend only through a portion of the total number of sheets 28.

Positioned at the base of the multi-layered absorbent structure 38 is one or more layers of absorbent tissue 48. In FIG. 3, two layers of absorbent tissue 48 are present. The tissue layers 48 are sized and shape to span the surface area of the multi-layered absorbent structure and provide a fluid reservoir within the sanitary napkin 32.

Returning to FIGS. 1 and 2, the multi-layered absorbent structure 16 has the central passage 26 formed therein which is perpendicularly aligned with the x-axis and is coaxially aligned with the z-axis. This central passage 26 fluidly communicates with various passages 50 present between each pair of folded sheets 24. The fluid passages 50 are formed by folding the sheet 24 to obtain the multi-layered absorbent structure 16. The central passage 26 also communicates with a passage 52 formed between the upper surface of the folded sheet 24 and the lower surface of the wrapped tissue layer 30 and also with a passage 54 formed between the upper surface of the wrapped tissue layer 30 and the lower surface of the transfer layer 20. Because of the presence of the passages 26, 50, 52 and 54, any body fluid which is deposited on the upper surface of the cover 12 will be able to flow downward and sideways in the x and y axes and be quickly distributed to the entire surface area of the multi-layered absorbent structure 16. This unique feature allows a plurality of thin tissue sheets having an overall thickness of under 5 mm to have an absorbent capacity of at least 20 grams, preferably at least 22 grams, and most preferably, more than 25 grams. The total absorbent capacity of the sanitary napkin 10 can be measured using the test method described later in this patent application.

The passages 26, 50, 52 and 54 are formed and arranged such that any point within the absorbent 16 is at a distance of less than about 2 mm, and preferably less than about 1 mm, away from one of the other passages. This permits the body fluid to be routed throughout the absorbent 16 and gives the fluid the ability to reach the opposite side edges, the longitudinally spaced ends and the four corner areas of the absorbent 16 very quickly.

The above absorbent capacity for the sanitary napkin 10 is obtained without the use of any superabsorbent. By superabsorbent is meant those superabsorbent materials usually employed in sanitary napkins, diaper, training pants, etc. including hydroxy functional polymers, hydrogel-forming polymers, cross-linked copolymers, etc. Such superabsorbents are normally supplied by such companies as Dow Chemical, Hoechst-Celanese, and Stockhausen, Inc.

Positioned between the baffle 14 and the absorbent 16 is a resilient layer 56. The resilient layer 56 can consist of one or more sheets of a flexible, closed cell polyethylene foam. The resilient layer 56 can have a thickness ranging from between 0.5 mm to about 1.5 mm. A preferred thickness for the resilient layer 56 is about 0.8 mm. An example of a foam that is useable in the sanitary napkin 10 is Cell-Aire® Foam, CA-30, having a thickness of $\frac{1}{32}$ of an inch (about 0.79 mm), and a density of 1.2 pounds per cubic foot. This particular foam is available from Sealed Air Corporation having an address of 7110 Sante Fe drive, Hodgkins, Ill. 60525. Another light weight polypropylene foam which is suitable for this invention is MicroFoam® available from Ametek Microfoam Division, Brandwine Four Building, Route 1 and 202, Chadds Ford, Pa. 19317.

The resilient layer 56 provides the sanitary napkin 10 with a resilient feature so that it is able to maintain it's original dimensions and also is able to return to it's original width after it is squeezed or compressed while being worn by a woman. The resilient layer 56 is important for it allows the sanitary napkin 10 to spring back to approximately it's original size even after the sanitary napkin 10 has been wetted by body fluid. This ability to return to it's original size or at least close to it's original dimensions reduces the time the sanitary napkin 10 is in the roped, bunched or twisted stage. By retaining it's original shape, the sanitary napkin 10 is less likely to experience leakage of body fluid.

It should be noted that construction adhesive can be used in the sanitary napkin 10 to attach and bond the various layers together. For example, construction adhesive can be used to bond the baffle 14 to the resilient layer 56 and to bond the resilient layer 56 to the cover 12. The presence of such adhesive and the amount use will depend upon one's personal preference.

The sanitary napkin 10 also includes two elongated strips 58 and 60 of garment adhesive which are secured to the bottom of the baffle 14. The adhesive strips 58 and 60 are spaced apart and function to attach the sanitary napkin 10 to the inner crotch portion of an undergarment during use. The garment adhesive 58 and 60 enable the sanitary napkin 10 to be properly aligned and retained relative to the user's vaginal opening so that maximum fluid protection can be obtained.

It should be noted that the two strips of garment adhesive 58 and 60 could be replaced with a single strip if desired. Alternatively, a swirl pattern of adhesive or some other type of adhesive pattern can also be used. The garment adhesive is of such a nature that it will allow the user to remove the sanitary napkin 10 and reposition it on her undergarment if needed. The garment adhesive is commercially available from National Starch and Chemical Company having an office located at 10 Finderne Avenue, Bridgewater, N.J. 08807.

In order to protect the two garment adhesive strips 58 and 60 from contamination prior to use, the adhesive strips 58 and 60 are protected by a releasable peel paper 62. The peel paper 62 can be a white Kraft paper coated on one side so that it can be released from a hot melt adhesive. The peel paper is designed to be removed by the user immediately before she attaches the sanitary napkin 10 onto the inner crotch portion of her undergarment.

Referring again to FIG. 3, one will notice that this embodiment also uses a resilient layer 56, two spaced apart bands or strips of garment adhesive 58 and 60, as well as a releasable peel paper 62. However, in this embodiment, the resilient layer 56 is positioned below the baffle 36 yet is enclosed by the cover 34.

Figure 4:
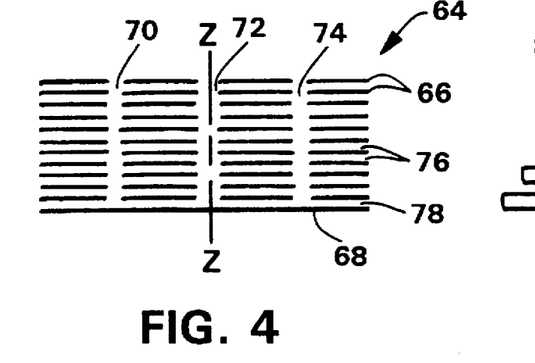
FIG. 4 is a schematic representation of another embodiment of the multi-layered absorbent structure showing a plurality of vertically stacked sheets having fluid passages formed therein.

Referring now to FIGS. 4–7, four alternative schematics are shown depicting different arrangements for a multi-layered absorbent structure. In FIG. 4, a multi-layered absorbent structure 64 is shown which includes a plurality of vertically stacked, horizontal sheets 66 positioned on top of at least one layer of tissue 68. Formed through the sheets 66 are at least three separate and distinct fluid passages 70, 72 and 74. The fluid passages 70, 72 and 74 are designed to permit the rapid transport of body fluid downward from the cover into the absorbent structure 64. The fluid passage 72 is perpendicularly aligned to the x-axis and coaxially aligned with respect to the z-axis. The fluid passages 70 and 74 are perpendicularly offset from the x-axis. Another way of stating this to say that the fluid passages 70 and 74 are aligned parallel to but spaced apart from the z-axis.

All three fluid passages 70, 72 and 74 communicate with fluid passages 76 formed between each pair of vertically stacked and horizontally aligned sheets 66 as well as with the fluid passage 78 formed between the tissue sheet 68 and the lower most sheet 66 of the multi-layered absorbent structure 64. The fluid passages 76 are formed by the void spaced created when two sheets 66 are positioned adjacent to one another. The vertical oriented fluid passages 70, 72 and 74 can be equally spaced apart or they can be randomly arranged. The passages 70, 72 and 74 can also be formed at an angle of between 0° to 180° relative to the x-axis, if desired. Each fluid passage 70, 72 and 74 can be the same size and shape or can be of a different size and/or shape. Each fluid passage 70, 72 and 74 can be an aperture, a hole, an opening, an orifice, a slit, a space, a division, a gap, a tear, etc. The fluid passages 70, 72 and 74 do not necessarily have to be formed in each sheet 66 but can instead be formed in at least some of the sheets 66. It should also be mentioned that each fluid passage 70, 72 and 74 can be formed at a different depth into the multi-layered absorbent structure 64. However, for maximum performance, each fluid passage 70, 72 and 74 should extend downward through the entire thickness of the multi-layered absorbent structure 64.

The multi-layered absorbent structure 64 can be formed such that any point within the absorbent 64 is at a distance of less than about 2 mm from one of the fluid passages 70, 72, 74, 76 and 78. This arrangement facilitate the movement of body fluid deposited on the cover down into the absorbent 64.

Figure 5:
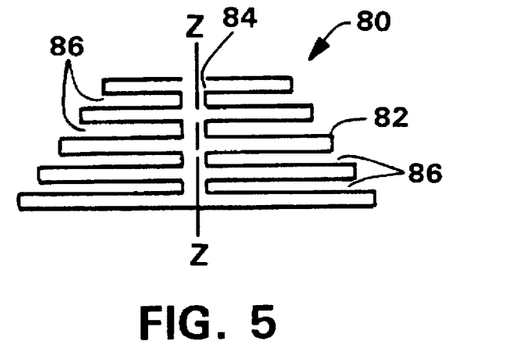
FIG. 5 is a schematic representation of another embodiment of the multi-layered absorbent structure showing a single sheet folded in an accordion fashion and having a polyhedron configuration with a central fluid passage formed therein.

Referring to FIG. 5, a multi-layered absorbent structure 80 is depicted having a triangular configuration about the z-axis. The multi-layered absorbent structure 80 is formed from a single sheet 82 of absorbent material, such as a tissue sheet, which is folded in an accordion fashion with a broad base which tapers to a narrower top. The multi-layered absorbent structure 80 contains a central fluid passage 84 which extends down from the top surface to the bottom base layer. The central fluid passage communicates with a plurality of horizontally aligned fluid passages 86 formed between the folded layer of the structure 80. This fluid passage arrangement permits body fluid deposited on the upper surface of the cover to quickly flow down into the multi-layered absorbent structure 80. It should also be noted that the body fluid can flow downward around the outer perimeter of the multi-layered absorbent structure 80 and still be directed into the horizontal oriented, fluid passages 86.

Figures 6, 7:
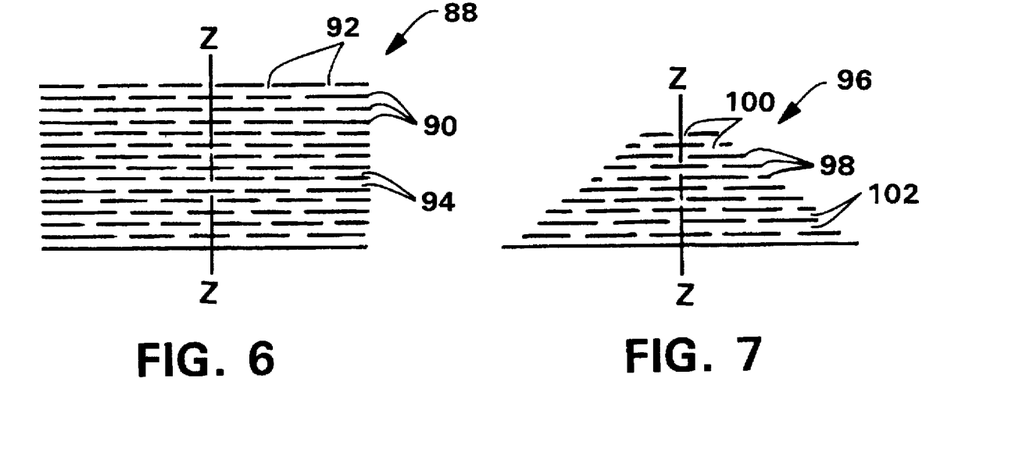
FIG. 6 is a schematic representation of another embodiment of the multi-layered absorbent structure showing a plurality of vertically stacked sheets arranged in a rectangular configuration with each sheet having at least one slit formed therein.
FIG. 7 is a schematic representation of still another embodiment of the multi-layered absorbent structure showing a plurality of vertically stacked sheets arranged in a triangular configuration with each sheet having at least one slit formed therein.

FIG. 6 is another embodiment of a multi-layered absorbent structure 88 having a rectangular configuration relative to the z-axis. The multi-layered absorbent structure 88 includes a plurality of vertically stacked, horizontal sheets 90 each having one or more slits or openings 92 formed therein. Preferably, each sheet 90 has a plurality of slits or openings 92 formed therein. The slits or openings 92 can be spaced apart from one another and can be uniformly or randomly arranged in each sheet 90. The vertical orientation of each slit or opening 92 relative to the slits or openings 92 formed through an adjacent sheet 90 can vary. Some slits or openings 92 can be coaxially aligned with the slits or openings 92 in an adjacent sheet 90 while other are offset from one another. The slits or openings 92 serve as fluid passages for routing body fluid deposited on the cover to the entire surface area of the multi-layered absorbent structure 88. For good fluid distribution, the slits or openings 92 can be arranged such that any point within the absorbent structure 88 is at a distance of less than about 2 mm away from one of the fluid passages 92. Preferably, any point within the absorbent structure 88 is at a distance of less than about 1 mm away from one of the fluid passages 92. When the slits or openings 92 are offset from one another in two adjacent sheets 90, a circuitous fluid route is presented which exposes a greater surface area of the multi-layered absorbent structure 88 into which the body fluid can be absorbed and retained.

As stated above, each of the slits or openings 92 fluidly communicates with a plurality of horizontal passages 94 formed between each pair of vertically stacked sheets 90. The vertical openings 92 fluidly communicate with the horizontal passages 94. This passage arrangement permits body fluid deposited on the upper surface of the cover to quickly flow down into the multi-layered absorbent structure 88. It should also be noted that the body fluid can flow downward around the outer perimeter of the multi-layered absorbent structure 88 and still be directed into the horizontal passages 94.

Referring to FIG. 7, still another embodiment of a multi-layered absorbent structure 96 is shown having a triangular configuration relative to the z-axis. The multi-layered absorbent structure 96 includes a plurality of vertically stacked sheets 98 each having one or more slits or openings 100 formed therein. Preferably, each sheet 98 has a one or more slits or openings 100 formed therein. The slits or openings 100 can be spaced apart from one another and can be uniformly or randomly arranged in each sheet 98. The vertical orientation of each slit or opening 100 relative to the slits or openings 100 formed through an adjacent sheet 98 can vary. Some slits or openings 100 can be coaxially aligned with the slits or openings 100 in an adjacent sheet 98 while other are offset from one another. When the slits or openings 100 are offset from one another in two adjacent sheets 98, a circuitous fluid route is presented which exposes a greater surface area of the multi-layered absorbent structure 96 into which the body fluid can be absorbed and retained.

As stated above, each of the slits or openings 100 fluidly communicates with a plurality of horizontal passages 102 formed between each pair of vertically stacked sheets 98. The vertical openings 100 fluidly communicate with the horizontal passages 102. This passage arrangement permits body fluid deposited on the upper surface of the cover to quickly flow down into the multi-layered absorbent structure 96. It should also be noted that the body fluid can flow downward around the outer perimeter of the multi-layered absorbent structure 96 and still be directed into the horizontal passages 102.

When an absorbent article is constructed having a multi-layered absorbent structure as taught above, it has been found that the absorbent article will perform exceptionally well when it also has certain characteristics. These characteristics are listed in Table 1 below. Three or more absorbent articles were tested to obtain the characteristics described above.

TABLE 1

|   |   | Code S | K-C Kotex® Ultra | J & J Sure & Natural® | J & J Stayfree® | P & G Always® Ultra |
|---|---|---|---|---|---|---|
| 1. | Crush | 21 | 14 | 12 | 12 | 16 |
|  | Recovery | 22 | 14 | 11 | 13 | 10 |
|  | (mm) | 20 | 13 | 10 | 12 | 14 |
|  |  |  | 13 |  |  |  |
|  |  |  | 13 |  |  |  |
|  | Average | 21 | 13.4 | 11 | 12.3 | 13.3 |
|  | Std. Dev. | 1 | 0.6 | 1 | 0.6 | 3.1 |
| 2. | Dry Load | 326.3 | 299.3 | 525.7 | 429.9 | 276.5 |
|  | (grams) | 383.2 | 371.0 | 471.6 | 429.6 | 227.2 |
|  |  | 346.1 | 336.4 | 464.2 | 363.6 | 271.6 |
|  |  |  | 346.3 | 488.9 |  |  |
|  |  |  | 294.3 |  |  |  |
|  | Average | 351.9 | 329.5 | 487.2 | 407.7 | 258.4 |
|  | Std. Dev. | 28.9 | 27.6 | 16.1 | 16.1 | 16.1 |
| 3. | Wet Load | 427.7 | 319.1 | 306.2 | 259.3 | 163.0 |
|  | (grams) | 348.6 | 264.6 | 316.1 | 303.7 | 138.0 |
|  |  | 321.4 | 230.0 | 348.8 | 371.0 | 153.4 |
|  |  |  | 306.7 |  |  |  |
|  | Average | 365.9 | 277.5 | 323.7 | 311.3 | 151.5 |
|  | Std. Dev. | 55.2 | 35.8 | 22.3 | 56.2 | 61.6 |
| 4. | Thickness | 4.0 | 3.7 | 3.1 | 2.8 | 2.6 |
|  | (mm) | 4.2 | 3.6 | 3.6 | 2.9 | 2.6 |
|  |  | 4.0 | 3.7 | 3.2 | 2.8 | 2.6 |
|  |  |  | 3.6 | 3.1 |  |  |
|  |  |  | 3.8 | 3.3 |  |  |
|  | Average | 4.1 | 3.7 | 3.2 | 2.8 | 2.6 |
|  | Std. Dev. | 0.1 | 0.1 | 0.2 | 0.1 | 0.0 |
| 5. | Stress | 82.4 | 82.0 | 169.4 | 154.1 | 107.2 |
|  | (g/mm) | 90.8 | 101.9 | 131.0 | 150.7 | 88.4 |
|  |  | 85.9 | 90.9 | 146.9 | 132.2 | 105.3 |
|  |  |  | 95.1 |  |  |  |
|  |  |  | 77.5 |  |  |  |
|  | Average | 86.4 | 89.5 | 149.0 | 145.7 | 100.3 |
|  | Std. Dev. | 4.2 | 10.0 | 19.1 | 11.8 | 10.3 |
| 6. | Absorbent | 27.3 | 22.9 | 57.4 | 40.7 | 43.0 |
|  | Capacity | 28.0 | 22.4 | 59.7 | 42.0 | 42.5 |
|  | (g) | 29.4 | 22.6 | 60.2 | 41.7 | 42.1 |
|  |  | 27.6 | 23.7 | 59.8 | 41.6 | 41.6 |
|  |  | 27.7 | 24.2 | 58.3 | 40.6 | 42.9 |
|  | Average | 28.0 | 23.1 | 59.1 | 41.3 | 42.4 |
|  | Std. dev. | 0.8 | 0.8 | 1.2 | 0.6 | 0.6 |

Note:
"K-C" is an abbreviation for Kimberly-Clark Corporation
"J & J" is an abbreviation for Johnson & Johnson
"P & G" is an abbreviation for Procter & Gamble
"Std Dev." is an abbreviation for Standard Deviation.

All of the absorbent articles to be tested for the characteristics identified above should be acclimated for at least two hours in a controlled environment at a temperature of 23° C.±1° C. (73.4° F.±1.8° F.) and a relative humidity of 50±2 percent.

The first characteristic that the absorbent article should have is a "crush recovery" value of at least about 15 mm, preferably at least 18 mm, and most preferably, 20 mm or above. The "crush recovery" value is measured using an apparatus 104 depicted in FIGS. 8 and 9. The apparatus 104 is designed to retain an absorbent article 106 having a pair of spaced apart longitudinal side edges 108 and 110. The absorbent article 106 also has an absorbent 107 with a pair of spaced apart longitudinal side edges 109 and 111. The side edges 109 and 111 can be coincidental with or spaced inward from the longitudinal side edges 108 and 110 of the absorbent article 106.

Figure 8:
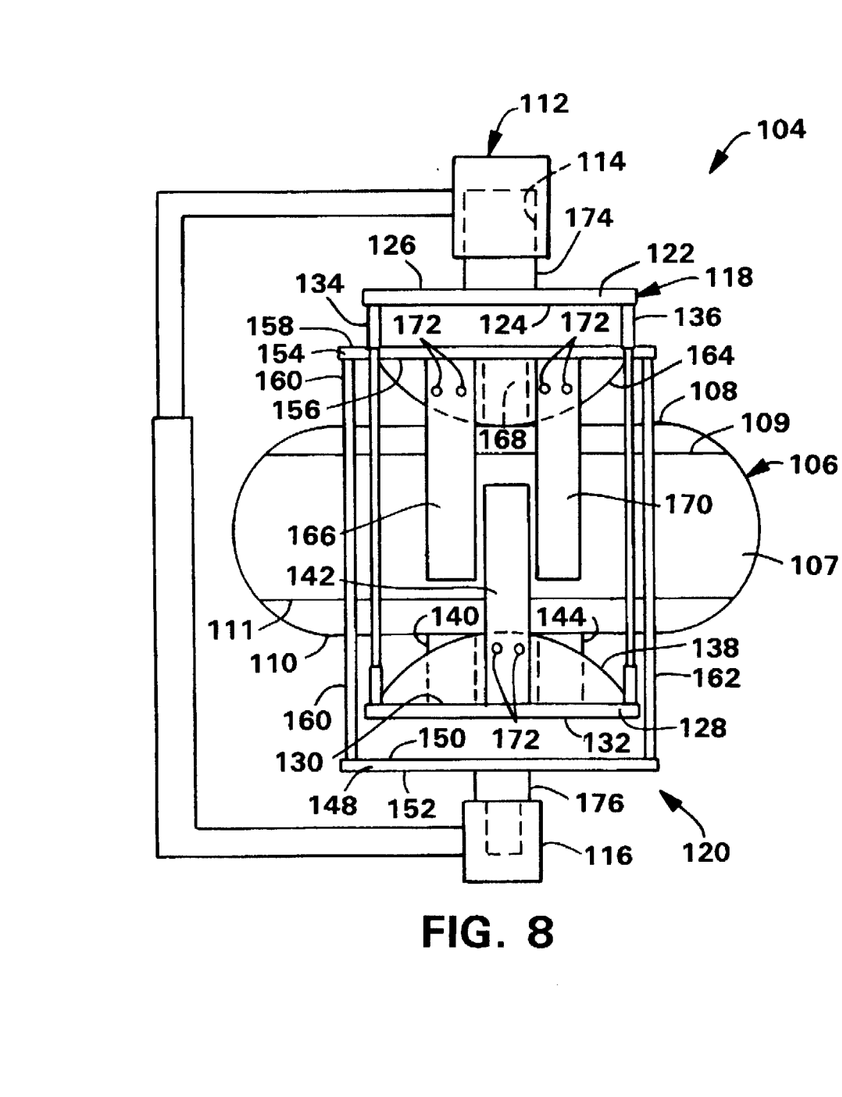
FIG. 8 is a front elevational view of an apparatus in an open position depicting a non-crushed absorbent article positioned between first and second frame members and attached to a tester.

Referring to FIG. 8, a tester 112 is depicted which is capable of measuring the force, in grams, required to crush the absorbent article 106 sideways. By sideways is meant along the transverse central y-axis which is shown in FIG. 1. The tester 112 includes first and second arms, 114 and 116 respectively, only one of which has to be movable. The first and second arms 114 and 116 are coaxially aligned and spaced apart. The distance to which the arms 114 and 116 are separated can be varied to accommodate the size of the apparatus 104 and the size of the absorbent article 106 which is to be tested. The tester 112 is capable of moving at least one of the arms 114 and/or 116 relative to the other arm at/a predetermined speed. One common tester which can be used is a Sintech® 1/S which is available from Sintech, a division of MTS Systems Corp. having an office at 1400 Technology Drive, Eden Prairie, Minn. 55344. A commercially available, alternative tester is an Instron® tester available from Instron Corporation having an office at 100 Royall Street, Canton, Mass. 02021.

Figure 9:
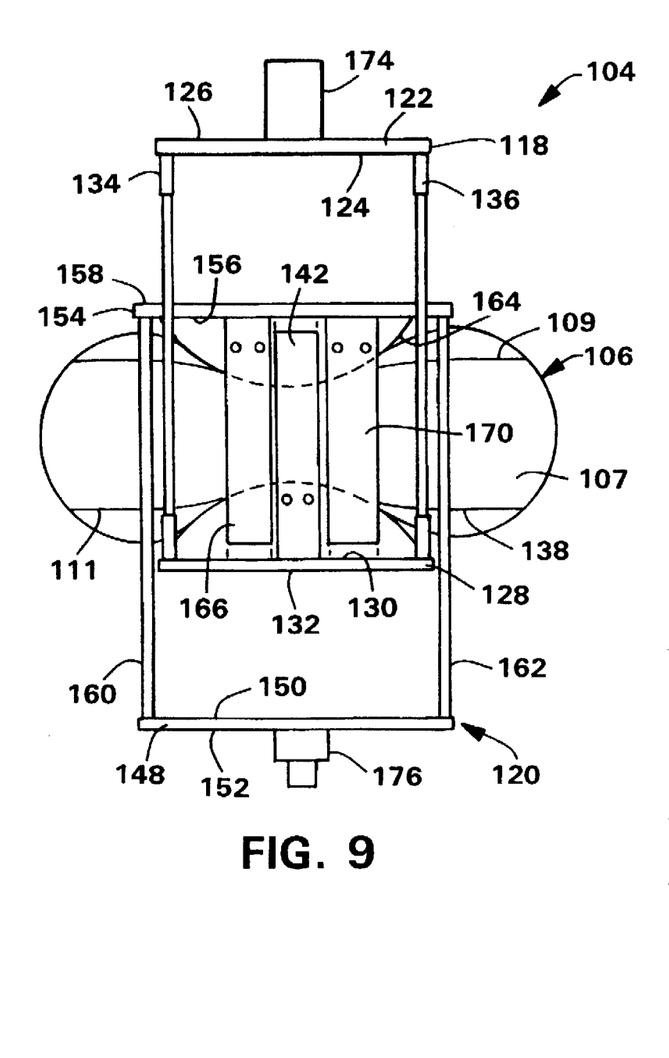
FIG. 9 is a front elevational view of the apparatus in a closed position depicting the absorbent article having been crushed sideways between first and second frame members.

The apparatus 104 includes a first frame member 118 and a second frame member 120 which are interleaved to operate in unison. The first frame member 118 and a second frame member 120 are reciprocally movable relative to one another. Both of the frame members, 118 and 120 respectively, can be rectangular in configuration. Other shapes may work equally as well. The first frame member 118 has a first plate 122 with an inner surface 124 and an outer surface 126. The first frame member 118 also has a second plate 128 with an inner surface 130 and an outer surface 132. The first and second plates, 122 and 128 respectively, are joined together by at least two support members 134 and 136, and preferably, by four support members.

In FIGS. 8 and 9, four support members are actually present but only the two support members, 134 and 136 respectively, are visible. The remaining two support members are located directly behind and at a distance from the two support members 134 and 136. When four support members are present, they can be arranged in a rectangular fashion such that each is connected to a corner of the first and second plates, 122 and 128 respectively.

Secured to or formed on the inner surface 130 of the second plate 128 is a shoulder 138. The shoulder 138 can have an arcuate shape and more preferably a semi-circular configuration having a radius of about 3 inches (about 76 mm). The semi-circular configuration of the shoulder 138 should have a smooth profile which contacts the central section of the longitudinal side edge 110 of the absorbent article 106. The shoulder 138 should have a fixed width depending upon the thickness of the absorbent article 106. The width of the shoulder 138 is measured along a line extending perpendicular to the plane of the sheet illustrating FIG. 8. The shoulder 138 should have a width of about 11 mm for an absorbent article which has a thickness or caliper ranging from between about 2 mm to about 7 mm. The shoulder 138 should have a width of about 7 mm for an absorbent article which has a thickness or caliper of less than about 2 mm and a width or thickness of about 17 mm for an absorbent article having a thickness or caliper of greater than about 7 mm. A method of measuring the thickness of an absorbent article 106 is described in explicit detail later in this application.

Extending outwardly from the shoulder 138 is at least one, preferably two, and more preferably three or more wands 140, 142 and 144. Each wand 140, 142, and 144 can be secured to the shoulder 138 and/or to the second plate 128 by a common fastener, for example by a pair of screws 146, as shown. Other fasteners, such as bolts, nuts, rivets, pins, etc. can also be used, as well as attachment by welding, fusion, adhesive, etc. These and other methods of attaching or securing the wands 140, 142 and 144 to the shoulder 138 and/or the first plate 122 are known to those skilled in the art.

The wands 140, 142 and 144 should be flexible members so as to be capable of bending outwardly as the absorbent article 106 gets thicker as it is crushed along the y-axis. The wands 140, 142 and 144 can be constructed of a pliable or bendable material such as plastic or rubber or they can be made from thin pieces of metal, wood, etc. For measuring the "crush recovery" value of a thin absorbent article, like a sanitary napkin, each wand 140, 142 and 144 can be a thin plastic strip having a length of about 3.5 inches (about 89 mm), a width of about ¾ of an inch (about 19 mm) and a thickness of about 1/16 of an inch (about 1.6 mm). The exact dimension can vary to suit one's particular absorbent article.

Each wands 140, 142 and 144 extends outwardly toward the first plate 122. The wands 140, 142 and 144 can be oriented parallel to one another and can be spaced apart so as not to interfere with one another. In FIGS. 8 and 9, the wands 140 and 144 are secured to one side of the shoulder 138 while the wand 142 is secured to the opposite side of the shoulder 138. This allows the wands 140, 142 and 144 to be offset from one another.

The second frame member 120 can be constructed to be very similar to or identical in configuration to the first frame member 118 except that it will have to be of a slightly different size so as to permit the two frame members 118 and 120 to be interleaved. By "interleaved" is meant that the first frame member 118 is assembled in such a fashion with the second frame member 120 that one can move relative to the other with being separated therefrom. The second frame member 120 has a third plate 148 with an inner surface 150 and an outer surface 152. The second frame member 120 also has a fourth plate 154 with an inner surface 156 and an outer surface 158. The third and fourth plates, 148 and 154 respectively, are joined together by at least two support members 160 and 162, and preferably, by four support members. The fourth plate 154 is so sized and shaped so as to be able to slide between the first and second plates, 122 and 128 respectively, of the first frame member 118.

In FIGS. 8 and 9, four support members are actually present but only the two support members 160 and 162 are visible. The remaining two support members are located directly behind the two support members 160 and 162. When four support members are present, they can be arranged in a rectangular fashion such that each is connected to a corner of the third and fourth plates, 148 and 154 respectively.

Secured to or formed on the inner surface 156 of the fourth plate 154 is a shoulder 164. The shoulder 164 can be arcuate in shape. More preferably, the shoulder 164 can have a semi-circular configuration, and should have a width identical to that described above for the shoulder 138. Extending outwardly from the shoulder 164 is at least one, preferably two, and more preferably three or more wands 166, 168 and 170. Each wand 166, 168, and 170 can be secured to the shoulder 164 and/or to the fourth plate 154 by a common fastener, for example a pair of screws 172, as shown. Other fasteners, such as bolts, nuts, rivets, pins, etc. can also be used, as well as attachment by welding, fusion, adhesive, etc. These and other methods of attaching or securing the wands 166, 168 and 170 to the shoulder 164 and/or the fourth plate 154 are known to those skilled in the art.

The wands 166, 168 and 170 can be similar or identical to the wands 140, 142 and 144 discussed above. Each wands 166, 168 and 170 extends outwardly toward the third plate 148. The wands 166, 168 and 170 can be oriented parallel to one another and can be spaced apart so as not to interfere with one another. In FIGS. 8 and 9, the wands 166 and 170 are secured to one side of the shoulder 164 while the wand 168 is secured to the opposite side of the shoulder 164. This allows the wands 166, 168 and 170 to be offset from one another.

The wands 140, 142 and 144 secured to the first frame member 118 intermesh with but do not physically contact the wands 166, 168 and 170 secured to the second frame member 120. However, actual rubbing contact between the wands 140, 142, 144, 166, 168 and 170 can occur if desired, but is not viewed to be advantageous. When the wands 140, 142 and 144 engage or intermesh with the wands 166, 168 and 170, in a similar fashion as when the fingers on a person right and left hands come together, an opening or defined area is formed into which the absorbent article 106 can be inserted. The absorbent article 106 is positioned between the first and second frame members, 118 and 120 respectively. In this position, the wands 140, 142, 144, 166, 168 and 170 are aligned parallel to one another with the wands 140 and 144 offset from wand 168 while wands 166 and 170 are offset from wand 168. With the wands 140, 142, 144, 166, 168 and 170 engaged, there will be three wands located on each side of the absorbent article 106.

The first frame member 118 further has an attachment mechanism 174, such as an outwardly extending shaft, secured to the outer surface 132 of the first plate 122. The shaft 174 can be releaseably attached to the first arm 114 of the tester 112. Likewise, the second frame member 120 has an attachment mechanism 176, such as an outwardly extending shaft, secured to the outer surface 152 of the third plate 148. The shaft 176 can be releaseably attached to the second arm 116 of the tester 112. With the apparatus 104 secured to the tester 112, movement of at least one of the arms 114 and 116 away from the other will cause the first frame member 118 to move relative to the second frame member 120. This will cause the two shoulders 138 and 164 to approach one another and squeeze the longitudinal side edges 108 and 110 of the absorbent article 106 thereby crushing the article 106 to a preselected distance between the shoulders 138 and 164.

The method of operating the apparatus 104 to crush an absorbent article 106 sideways along the y-axis is as follows: first, the apparatus 104 is secured in the tester 112, preferably in a vertical orientation. When secured, the first and second frame members, 118 and 120 respectively, of the apparatus 104 are attached to the two arms 114 and 116 of the tester 112. The first and second frame members, 118 and 120 respectively, are adjusted to be a predetermined distance apart, for example 4 inches (about 102 mm). The 4 inch (about 102 mm) setting allows the absorbent article 106 to be positioned between the first and second frame members, 118 and 120 respectively, while still in a planar or non-buckled condition. A pre-calibrated load cell, for example, a 50 pound full scale, tension/compression load cell, is utilized.

Second, any wings, flaps, panels, tabs or appendages which may be attached to or integrally formed with the absorbent article 106 should be removed before the absorbent article 106 is tested. Such laterally extending wings, flaps, panels, tabs or appendages can be removed prior to testing, by cutting them off along a line approximately parallel to the longitudinal side edges 108 and 110 of the absorbent article 106. Third, the absorbent article 106 is wetted with 25 cc of 0.9 percent by weight saline. This can be done by pouring the saline onto the center of the bodyside surface of the absorbent article 106 at a rate slow enough to allow all of the saline to be absorbed by the article 106. Fourth, the wetted absorbent article 106 is then centered in the apparatus 104 as indicated in FIG. 8. Fifth, the load cell of the tester 112 is zeroed per the manufacturer's instructions. Sixth, the tester is then actuated causing the arms 114 and 116 to be separated at a predetermined rate. The actual "crush recovery" values listed in Table 1 where obtained using a rate of 12 inches/minute (304.8 mm/minute). This action causes the longitudinal side edges 108 and 110 of the absorbent article 106 to be crushed toward one another between the shoulders 138 and 164. The tester 112 will measure and record the load exerted on the absorbent article 106 as it is being crushed. The tester 112 should be programmed to stop when the first and second frame members, 118 and 120 respectively, are a set distance apart, for example, 1.5 inches (38 mm), see FIG. 9, when testing a sanitary napkin. The maximum force applied during the test is measured and recorded. This is the "wet load" value which will be discussed below.

After the absorbent article 106 has been crushed, the arms 114 and 116 of the tester 112 are retracted to their original pretest position. In this position, the longitudinal side edge 110 of the absorbent article 106 is contacting the first shoulder 138 and the opposite longitudinal side edge 108 is spaced apart from the second shoulder 164. This arrangement allows the absorbent article 106 to freely recover toward its original transverse dimension. After approximately 30 seconds, the recovered width is measured in millimeters. The recovered width is the distance between the longitudinal side edges 109 and 111 of the absorbent 107. The "crush recovery" value is this measured recovered width minus the distance to which the absorbent article 106 was crushed, for example 1.5 inches (about 38 mm) for the samples recorded in Table 1. There will be a "crush recovery" value for each absorbent article 106 tested.

The maximum load, measured in grams, during the above-identified test is referred to as the "wet load" value. A second characteristic which the absorbent article 106 should exhibit is a high "wet load" value. The "wet load" is a measure of the ability of an absorbent article to resist deformation after it has absorbed a given quantity of fluid. Many thin absorbent articles display a tendency to bunch, twist or rope after they absorb a certain quantity of body fluid. Such configurations create a high probability that the absorbent article will leak as additional body fluid contacts the bodyside cover. By constructing an absorbent article with a predetermined "wet load" value, one can minimize the tendency of the article to bunch, twist or rope. The absorbent article 106 should have a "wet load" value of at least about 300 grams, preferably at least about 320 grams, and most preferably at least about 350 grams or above.

A third characteristic of the absorbent article is that it should have a thickness or caliper of less than about 5 millimeters, preferably, from between about 3 mm to 5 mm, and most preferably, from between about 4 mm to about 5 mm. The thickness is measured by plating a lucite block, measuring 0.5 of an inch by 1.75 inches (12.7 mm by 44.5 mm) on top of the absorbent article 106. The thickness is determined with an indicator gauge that measures the distance of the block above a flat surface. The block is placed with one of the 1.75 inch (about 44.5 mm) long edges along one of the long edges of the absorbent core 107 of the absorbent article 106, with all of the block itself being on top of the absorbent core 107. The block is roughly centered along the length of the absorbent article 106. The height of the absorbent article 106 plus the block, is then subtracted from the height of the block alone on the surface, to give the thickness of the absorbent article 106.

A fourth characteristic of the absorbent article is that it should exhibit a low "stress value." The "stress value" of an absorbent article is defined as the "dry load" divided by the "thickness." The "dry load" is obtained by running a test identical to that described above for "wet load" except that the absorbent article 106 is not wetted with saline. The smaller the stress value the more comfortable the absorbent article will be in use. The absorbent article should have a "stress value" of less than about 100 grams/mm, preferably less than about 90 grams/mm, and most preferably less than about 85 grams/mm.

A fifth characteristic of the absorbent article 106 is that it should have an absorbent capacity of at least 20 grams, preferably, above about 25 grams, and most preferably, above about 27 grams. The absorbent capacity of an absorbent article is measured as follows: The absorbent article is allowed to become saturated in an excess of 0.9 percent by weight saline for five minutes. It is then placed face down on the grid of a vacuum box, and covered with a rubber mat to make a vacuum seal. A 0.5 psi vacuum is pulled through the grid for approximately 5 minutes, to extract excess saline from the absorbent article. The amount of saline remaining in the absorbent article after vacuum extraction is the measured absorbent capacity.

While the invention has been described in conjunction with a specific embodiment, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An apparatus comprising:
   a) a tester having first and second arms, at least one of which is movable, said arms capable of causing controlled movement at a predetermined speed of a device attached therebetween and means for measuring the force required for said controlled movement;
   b) a first frame member attached at one end to said first arm, said first frame member having a shoulder with a first flexible member extending outwardly therefrom; and
   c) a second frame member attached at one end to said second arm, said second frame member having a shoulder with a second flexible member extending outwardly therefrom, said first and second frame members being arranged such that said first and second flexible members are spaced apart to enable an absorbent article to be positioned therebetween, and movement of said first frame member relative to said second frame member causes said absorbent article to be crushed in a sideways direction between said shoulders.

2. The apparatus of claim 1 wherein said first frame member has an outwardly extending shaft which can be releaseably attached to said first arm and said second frame member has an outwardly extending shaft which can be releaseably attached to said second arm.

3. The apparatus of claim 1 wherein said first and second members are plastic.

4. The apparatus of claim 1 wherein said first and second flexible members are aligned parallel to one another.

5. The apparatus of claim 1 wherein said first and second flexible members are offset from one another.

6. The apparatus of claim 1 wherein said first frame member has an arcuately shaped shoulder with at least two flexible members extending outwardly therefrom.

7. The apparatus of claim 1 wherein said second frame member has an arcuately shaped shoulder with at least two flexible members extending outwardly therefrom.

8. The apparatus of claim 1 wherein said first and second frame members are reciprocally moveable relative to one another.

9. An apparatus comprising:
 a) a tester having first and second arms which are coaxially aligned and spaced apart, at least one of said arms being movable, said arms capable of causing controlled movement at a predetermined speed of a device attached therebetween and means for measuring the force required for said controlled movement;
 b) a first rectangular frame member attached at one end to said first arm, said first frame member having a shoulder with a first flexible member extending outwardly therefrom; and
 c) a second rectangular frame member attached at one end to said second arm, said second frame member having a shoulder with a second flexible member extending outwardly therefrom, said first and second frame members being arranged such that said first and second flexible members are spaced apart to enable an absorbent article to be positioned therebetween, and movement of said first frame member relative to said second frame member causes said absorbent article to be crushed in a sideways direction between said shoulders.

10. The apparatus of claim 9 wherein said first frame member has an outwardly extending shaft which can be releaseably attached to said first arm and said second frame member has an outwardly extending shaft which can be releaseably attached to said second arm.

11. The apparatus of claim 9 wherein said first frame member has an arcuately shaped shoulder with at least two flexible members extending outwardly therefrom.

12. The apparatus of claim 9 wherein said second frame member has an arcuately shaped shoulder with at least two flexible members extending outwardly therefrom.

13. The apparatus of claim 9 wherein said first and second frame members are reciprocally moveable relative to one another.

14. An apparatus comprising:
 a) a first frame member having first and second spaced apart plates secured together by four support members, each plate having an inner surface and an outer surface, a first thin plastic strip extending outwardly from said second plate, and an attachment mechanism secured to said outer surface of said first plate for connection to a tester; and
 b) a second frame member having third and fourth spaced apart plates secured together by four support members, each plate having an inner surface and an outer surface, and a second thin plastic strip extending outwardly from said fourth plate, said second frame member being sized to permit said fourth plate to move between said first and second plates of said first frame member such that an absorbent article positioned between said first and second thin plastic strips can be crushed to a predetermined dimension, and an attachment mechanism secured to said outer surface of said third plate for connection to said tester such that said first and second frame members can be axially moved relative to one another.

15. The apparatus of claim 14 wherein said first frame member has a rectangular configuration.

16. The apparatus of claim 14 wherein said second frame member has a rectangular configuration.

17. The apparatus of claim 14 wherein said first frame member has three thin plastic strips attached thereto and said second frame member has three thin plastic strips attached thereto, said thin plastic strips intermeshing to form an area between said second and fourth plates into which an absorbent article can be positioned.

* * * * *